US012616404B1

(12) United States Patent
VanWyk et al.

(10) Patent No.: US 12,616,404 B1
(45) Date of Patent: May 5, 2026

(54) MISMATCH COMPENSATION FOR BIOSENSOR ELECTRODES

(71) Applicant: Meta Platforms Technologies, LLC, Menlo Park, CA (US)

(72) Inventors: Eric VanWyk, Seattle, WA (US); Brendan Patrick Flynn, Redmond, WA (US); Pinghung Wei, Kirkland, WA (US); Filipp Demenschonok, Bothell, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 761 days.

(21) Appl. No.: 18/047,539

(22) Filed: Oct. 18, 2022

(51) Int. Cl.
| | |
|---|---|
| *A61B 5/25* | (2021.01) |
| *A61B 5/00* | (2006.01) |
| *A61B 5/0537* | (2021.01) |
| *H03H 7/38* | (2006.01) |
| *A61B 5/291* | (2021.01) |
| *A61B 5/296* | (2021.01) |

(52) U.S. Cl.
CPC .............. *A61B 5/25* (2021.01); *A61B 5/0537* (2013.01); *A61B 5/7225* (2013.01); *H03H 7/38* (2013.01); *A61B 5/291* (2021.01); *A61B 5/296* (2021.01); *A61B 2562/0214* (2013.01)

(58) Field of Classification Search
CPC ... H03H 7/38; H03H 7/40; A61B 5/25; A61B 5/0537; A61B 5/7225; A61B 5/291; A61B 5/296; A61B 2562/0214
See application file for complete search history.

(56) References Cited

U.S. PATENT DOCUMENTS

| | | | |
|---|---|---|---|
| 10,368,760 B2 * | 8/2019 | Hauck | A61B 5/6885 |
| 10,555,686 B1 * | 2/2020 | Kimoto | A61B 5/0535 |
| 2020/0187823 A1 * | 6/2020 | Lepak | A61B 5/0531 |

FOREIGN PATENT DOCUMENTS

WO      WO-2022217322 A1 * 10/2022      ............. A61B 5/263

* cited by examiner

*Primary Examiner* — John W Poos
(74) *Attorney, Agent, or Firm* — Morgan, Lewis & Bockius LLP

(57)      ABSTRACT

The disclosed computer-implemented method may include measuring one or more electrical properties from a plurality of electrodes for biosignal measurement, determining, based on the measured one or more electrical properties, an impedance mismatch between at least a first electrode and a second electrode of the plurality of electrodes, and reducing the impedance mismatch by modulating an impedance of the first electrode. Various other methods, systems, and computer-readable media are also disclosed.

20 Claims, 9 Drawing Sheets

100

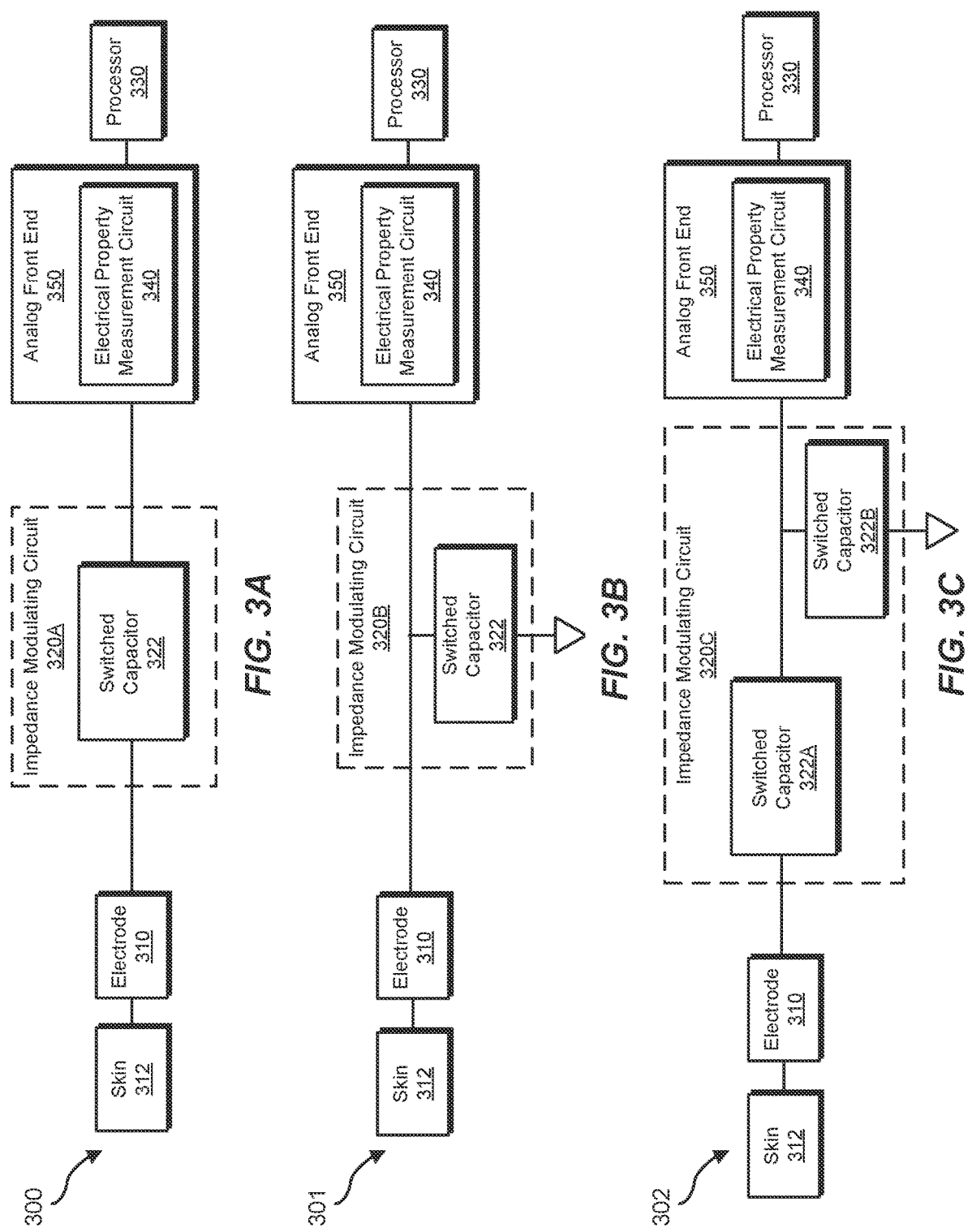

Method
400

800

820

810

820  830

810

MISMATCH COMPENSATION FOR BIOSENSOR ELECTRODES

BRIEF DESCRIPTION OF THE DRAWINGS

The accompanying drawings illustrate a number of exemplary embodiments and are a part of the specification. Together with the following description, these drawings demonstrate and explain various principles of the present disclosure.

FIGS. 3A-C are diagrams of example variable impedance circuits for biosensor devices.

Figure 1:
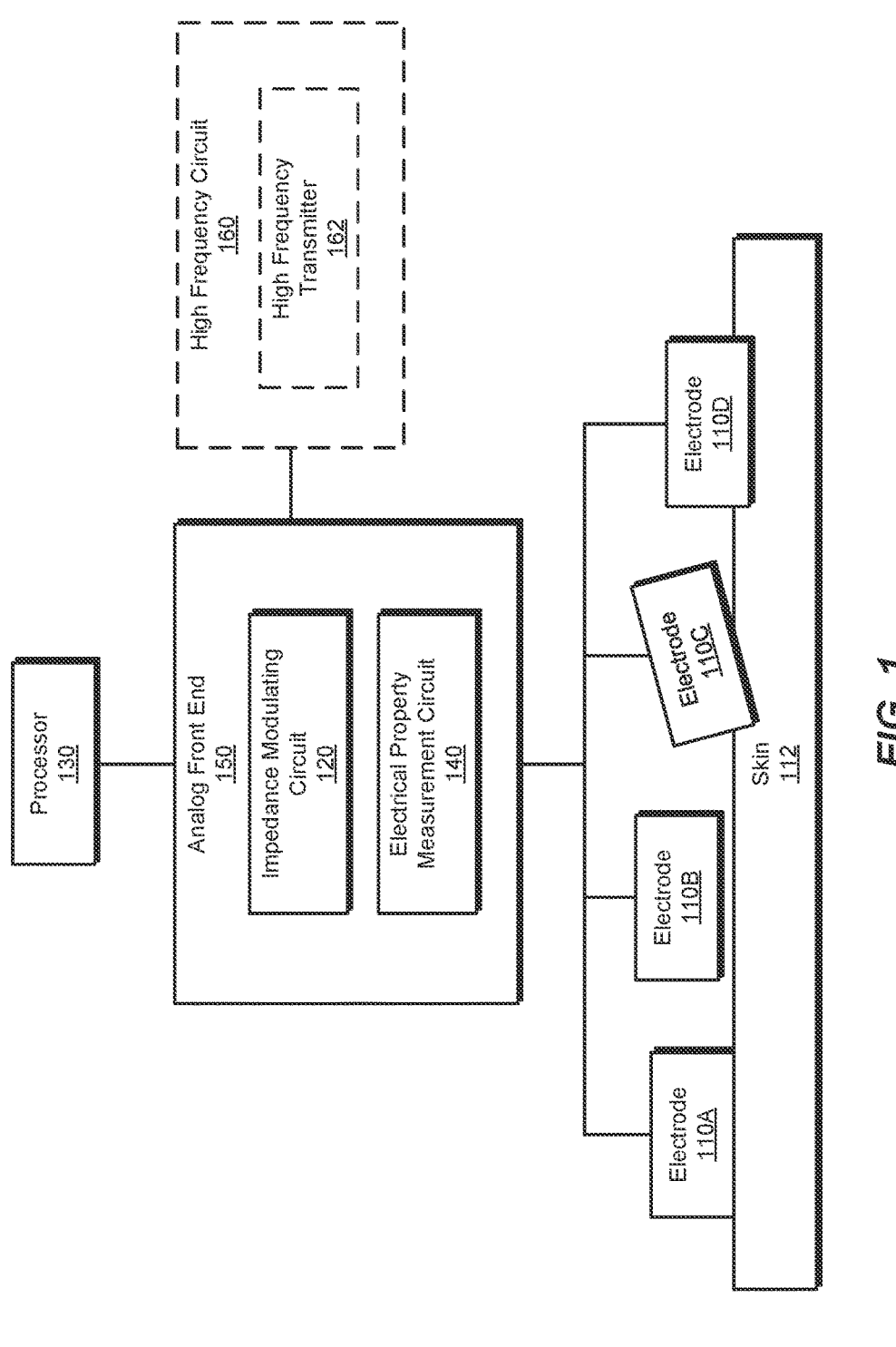
FIG. 1 is a diagram of an exemplary biosensor electrode environment.

Throughout the drawings, identical reference characters and descriptions indicate similar, but not necessarily identical, elements. While the exemplary embodiments described herein are susceptible to various modifications and alternative forms, specific embodiments have been shown byway of example in the drawings and will be described in detail herein. However, the exemplary embodiments described herein are not intended to be limited to the particular forms disclosed. Rather, the present disclosure covers all modifications, equivalents, and alternatives falling within the scope of the appended claims.

DETAILED DESCRIPTION OF EXEMPLARY EMBODIMENTS

Electromyography (EMG) devices and other biosensing or biosignal measurement devices (e.g., electrocardiograms (ECG), electroencephalograms (EEG), etc.) may measure electrical activity of a human body. Biosensing devices may measure EMG and other electrical signals emitted by the human body to measure certain aspects of the body, such as in a medical diagnostic context. These electrical signals may also be used as inputs for input devices of computing devices. These electrical signals are often small, for example in an order of magnitude of micro-volts.

Due to the precision necessary for accurate measurements, any noise may greatly influence accuracy. Biosensing measurements may further be influenced by the electrical properties of the biosensing devices themselves. For example, the electrodes of the biosensing devices may exhibit different electrical properties such that the inputs from the electrodes may be unbalanced. The unbalanced inputs may introduce noise. In some cases, the high variability of the skin-electrode interface may cause the unbalance. Thus, electrically balancing the electrodes for biosensing may reduce noise and improve measurement accuracy.

The present disclosure is generally directed to mismatch compensation for biosensor electrodes. As will be explained in greater detail below, embodiments of the present disclosure may measure electrical properties from electrodes for biosignal measurement, determine an impedance mismatch between two of the electrodes, and reduce the impedance mismatch by modulating an impedance of at least one of the two electrodes. By modulating the impedances of electrodes, impedance mismatches can be better balanced to reduce noise in biosignal measurement.

Features from any of the embodiments described herein may be used in combination with one another in accordance with the general principles described herein. These and other embodiments, features, and advantages will be more fully understood upon reading the following detailed description in conjunction with the accompanying drawings and claims.

The following will provide, with reference to FIGS. 1-5, detailed descriptions of systems and methods for compensating for mismatches in electrical properties between biosensor electrodes. Detailed descriptions of an example skin-electrode interface are provided in connection with FIG. 1. Detailed descriptions of example impedance modulating circuits are provided in connection with FIGS. 2A-C and 3A-C. Detailed descriptions of an example method for mismatch compensation for biosensor electrodes are provided in connection with FIG. 4. Detailed descriptions of a noise spectrum are provided in connection with FIG. 5.

FIG. 1 illustrates a biosensing device 100 and an example skin-electrode interface with a skin 112 of a user. As illustrated in FIG. 1, biosensing device 100 may include one or more electrodes 110 (e.g., an electrode 110A, an electrode 110B, an electrode 110C, and an electrode 110D), an analog front end 150 which may include an electrical property measurement circuit 140 and an impedance modulating circuit 120, and a processor 130. Electrodes 110A-D may correspond to biosensing electrodes capable of biosensor measurements by direct and/or indirect application to skin 112. Analog front end 150 may include circuitry for measuring and/or analyzing biosignals (e.g., electrical signals) detected by electrodes 110A-D. Electrical property measurement circuit 140 may correspond to circuitry for measuring and/or analyzing electrical properties of electrodes 110A-D. Impedance modulating circuit 120 may correspond to circuitry for modulating impedances of electrodes 110A-D, as will be described further herein. Processor 130 may correspond to a processor, controller, microcontroller (e.g., a microcontroller unit), and/or other logic circuitry that may control, for example, impedance modulating circuit 120.

The skin-electrode interface may cause variations in electrical properties amongst electrodes 110A-D. One or more of electrodes 110A-D may be placed on or applied to skin 112 in a suboptimal fashion that may affect the electrode's electrical properties and reduce an effectiveness of the electrode. For example, electrode 110B may be offset from skin 112 so as to not correctly contact skin 112. Electrode 110C may be biased to one side such that electrode 110C is not evenly contacting skin 112. Electrode 110D may be overly depressed into skin 112. In addition, although electrode 110A may be optimally placed on skin 112, variations in skin 112 itself (e.g., moisture/dryness, salt, use of gel, presence of hair, etc.) may cause electrical variances with respect to another optimally placed electrode. For example, the skin-electrode interface may cause high impedances and/or changing impedances over time for electrodes 110.

Electrical property measurement circuit 140 may include circuitry for measuring one or more electrical properties, directly and/or indirectly, of one or more of electrodes 110.

For example, electrical property measurement circuit 140 may directly measure impedances of one or more electrodes 110. In other examples, electrical property measurement circuit 140 may indirectly such as by measuring a biosignal using electrodes 110 and deriving or predicting impedances for each of electrodes 110 (e.g., based on comparison to a reference signal or a common mode signal or a separately injected AC signal or view analysis of a noise spectrum). In some examples, electrical property measurement circuit 140 may measure and/or predict impedance mismatches (e.g., relative impedance values). In some examples, electrical property measurement circuit 140 may iteratively predict impedance mismatches (e.g., by re-predicting the impedance mismatch after an impedance modulation based on a prior prediction). Although FIG. 1 illustrates electrical property measurement circuit 140 as a component of analog front end 150, in other examples, electrical property measurement circuit 140 may be fully integrated with analog front end 150 (e.g., as part of a signal measurement circuit) and/or may be a separate circuit from analog front end 150.

In a differential input system such as biosensing device 100, impedance mismatches between differential electrodes may reduce performance. Signals may be injected into skin 112 for reducing noise. However, mismatched impedances amongst electrodes 110 may cause the injected signals to appear as additional noise. For example, noise reduction techniques for reducing power line interference (PLI) noise (e.g., noise caused from electromagnetic interference from nearby power lines), common-mode noise (e.g., noise causing an offset to a common-mode or common voltage between electrodes), and/or other noise often include injecting signals to cancel the noise and/or using amplifiers. However, mismatched impedances may cause such techniques to appear as noise in measured signals.

By measuring the impedances of electrodes 110, impedance modulating circuit 120 may modulate the impedances of one or more of electrodes 110 to reduce the mismatches which may further reduce an amount of common mode to differential noise conversion. For example, impedance modulating circuit 120 may modulate the impedances of one or more of electrodes 110 by improving (e.g., artificially decreasing) the impedance and/or increasing the impedance. In some examples, impedance modulating circuit 120 may use real and/or imaginary impedances to tune the skin-electrode impedance in a band of frequencies and/or at a particular frequency. In some examples, impedance modulating circuit 120 may include a respective circuit for individual electrodes (see, e.g., FIGS. 2A-2C and 3A-3C), as will be discussed further below. In other examples, impedance modulating circuit 120 may modulate impedances of more than one of electrodes 110. In addition, impedance modulating circuit 120 may include a processor or controller or may be coupled to processor 130.

In some examples, to improve measurements and/or overall system performance, processor 130 may be configured to evaluate one or more of electrodes 110. For example, one or more of electrodes 110 may be selected as a reference electrode that may correspond to an electrode having desirable electrical properties for comparison with the other electrodes. Although in some examples the reference electrode may correspond to an electrode with better performance than the other electrodes, in other examples, the reference electrode may correspond to an electrode having electrical properties capable of being achieved with the other electrodes (e.g., via adjustment). In addition, processor 130 may select one or more of electrodes 110 as a weak electrode that may be disregarded. A weak electrode may be disregarded by shutting off the weak electrode (e.g., stopping measurements with the weak electrode), or ignoring measurements from the weak electrode. Although in some examples the weak electrode may correspond to an electrode with poorer performance than the other electrodes, in other examples, the weak electrode may correspond to an electrode having electrical properties that may not be readily adjusted (e.g., to approximately match the reference electrode).

In some examples, processor 130 may apply one or more machine learning models to determine the reference electrode and/or weak electrodes. For example, processor 130 may analyze using machine learning the electrical properties, measured signals, etc. of electrodes 110 to determine the reference electrode and/or weak electrodes.

In some examples, biosensing device 100 may include a high frequency transmitter 162 (which may inject a high frequency signal into skin 112) as part of a high frequency circuit 160 used in conjunction with electrodes 110 (e.g., measuring a high frequency response to the injected high frequency signal) for user inputs, such a tracking gestures and/or move data. To also use electrodes 110 as low frequency biosensors (e.g., with analog front end 150), impedance modulating circuit 120 may act as a frequency down-converter and/or a sub-sampler to selectively take portions of a spectrum of a measured signal into or out of an input range for analog front end 150. For example, impedance modulating circuit 120 may be used to move the high frequency portions of the measured signal outside of the input range of analog front end 150 and/or high frequency circuit 160 such that the high frequency portions are effectively ignored so as not to affect the biosignal. In another example, impedance modulating circuit 120 may move the high frequency portions within the input range of analog front end 150 and/or high frequency circuit 160 but above the biosignal frequency range such that both the high frequency portion and the biosignal frequency portion may be measured simultaneously. In yet another example, impedance modulating circuit 120 may move the high frequency portion on top of the biosignal frequency portion to effectively override the comparably weaker biosignal and use a full range of analog front end 150 for analyzing the signal.

Figures 2A, 2B, 2C:
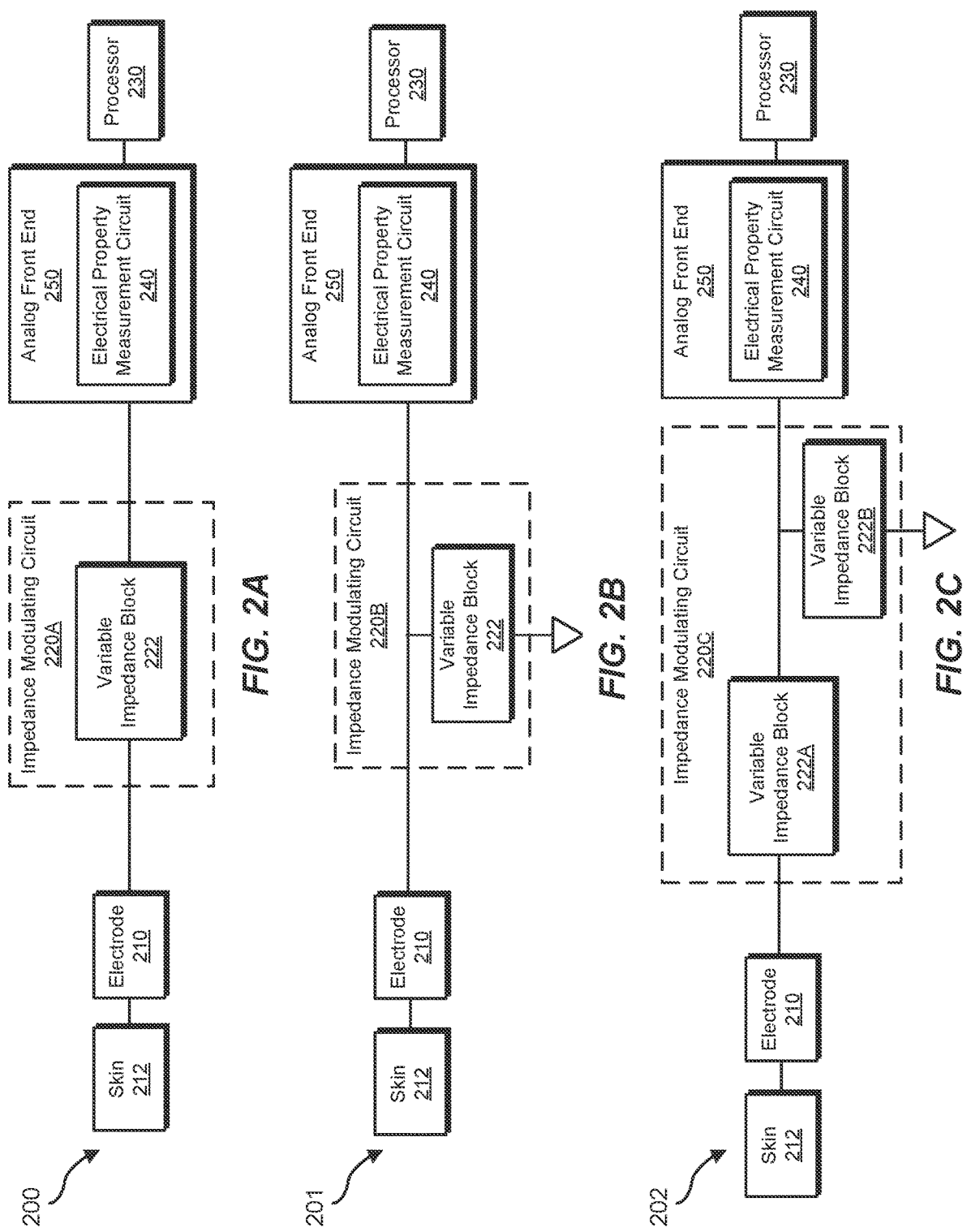
FIGS. 2A-C are diagrams of example variable impedance circuits for biosensor devices.

Turning now to example impedance modulating circuits, FIGS. 2A-2C illustrate example impedance modulating circuits for biosensing devices. FIG. 2A illustrates a biosensing device 200, which may correspond to biosensing device 100, interfacing with a skin 212, which may correspond to skin 112. Biosensing device 200 may include an electrode 210, which may correspond to electrode 110, an impedance modulating circuit 220A, which may correspond to impedance modulating circuit 120, an analog front end 250, which may correspond to analog front end 150, and a processor 230, which may correspond to processor 130.

As illustrated in FIG. 2A, impedance modulating circuit 220A may include a variable impedance block 222 that may modulate an impedance of electrode 210 to compensate for an impedance mismatch with another electrode (e.g., a reference electrode). Variable impedance block 222 may include one or more components, such as a capacitor, resistor, shunts, transistors, variable resistors, switched capacitors, passive tunable integrated circuits (PTICs), varactor diodes, switched capacitor networks, other networks, etc. for modulating the impedance of electrode 210. As illustrated in FIG. 2A, impedance modulating circuit 220A (e.g., variable impedance block 222) may be placed between electrode 210 and analog front end 250 to provide mismatch compensation before a signal from electrode 210 reaches a first stage of analog front end 250.

FIG. 2A illustrates variable impedance block 222 in a series configuration (e.g., in serial connection with electrode 210), although in other implementations variable impedance block 222 may be connected in a different configuration, such as a shunt configuration as in FIG. 2B. FIG. 2B illustrates another example biosensing device 201, which may correspond to biosensing device 200. Biosensing device 201 may include an impedance modulating circuit 220B, which may correspond to impedance modulating circuit 120. As illustrated in FIG. 2B, variable impedance block 222 may be configured in a shunt configuration (e.g., connected between signal and return lines).

The impedance modulating circuit may include various configurations of variable impedance blocks. For example, FIG. 2C illustrates biosensing device 202, which may correspond to biosensing device 200 and/or biosensing device 201. Biosensing device 202 may include an impedance modulating circuit 220C, which may correspond to impedance modulating circuit 120. Impedance modulating circuit 220C may include a variable impedance block 222A in a series configuration and a variable impedance block 222B in a shunt configuration. Having both variable impedance block 222A in a series configuration and variable impedance block 222B in a shunt configuration may provide additional tunability (e.g., enabling modulation over a broader frequency range).

In some examples, a variable impedance block may be implemented with a switched capacitor (e.g., a capacitor connected to a switch), as in FIG. 3. FIGS. 3A-3C illustrate example impedance modulating circuits for biosensing devices. FIG. 3A illustrates a biosensing device 300, which may correspond to biosensing device 100, interfacing with a skin 312, which may correspond to skin 112. Biosensing device 300 may include an electrode 310, which may correspond to electrode 110, an impedance modulating circuit 320A, which may correspond to impedance modulating circuit 120, an analog front end 350, which may correspond to analog front end 150, and a processor 330, which may correspond to processor 130.

FIG. 3A illustrates biosensing device 300 that may have impedance modulating circuit 320A with a switched capacitor 322 in a series configuration. FIG. 3B illustrates another example of a biosensing device 301, which may correspond to biosensing device 100. Biosensing device 301 may include an impedance modulating circuit 320B with switched capacitor 322 in a shunt configuration. FIG. 3C illustrates another example of a biosensing device 302, which may correspond to biosensing device 100. Biosensing device 302 may include an impedance modulating circuit 320C having a switched capacitor 322A in a series configuration and a switched capacitor 322B in a shunt configuration.

As described above, impedance modulating circuit 320C may include additional switched capacitors 322 in series and/or shunt configurations to provide modulation for additional frequencies. For example, impedance modulating circuit 320C may be used as a frequency down converter or sub-sampler as described herein. Thus, impedance modulating circuit 320C may provide impedance modulation for electrode 310 (e.g., to reduce an impedance mismatch with respect to a reference electrode) as well as selectively place portions (e.g., a specific frequency and/or range of frequencies) of an input signal's spectrum in and/or out of an input range of analog front end 350.

Figure 4:
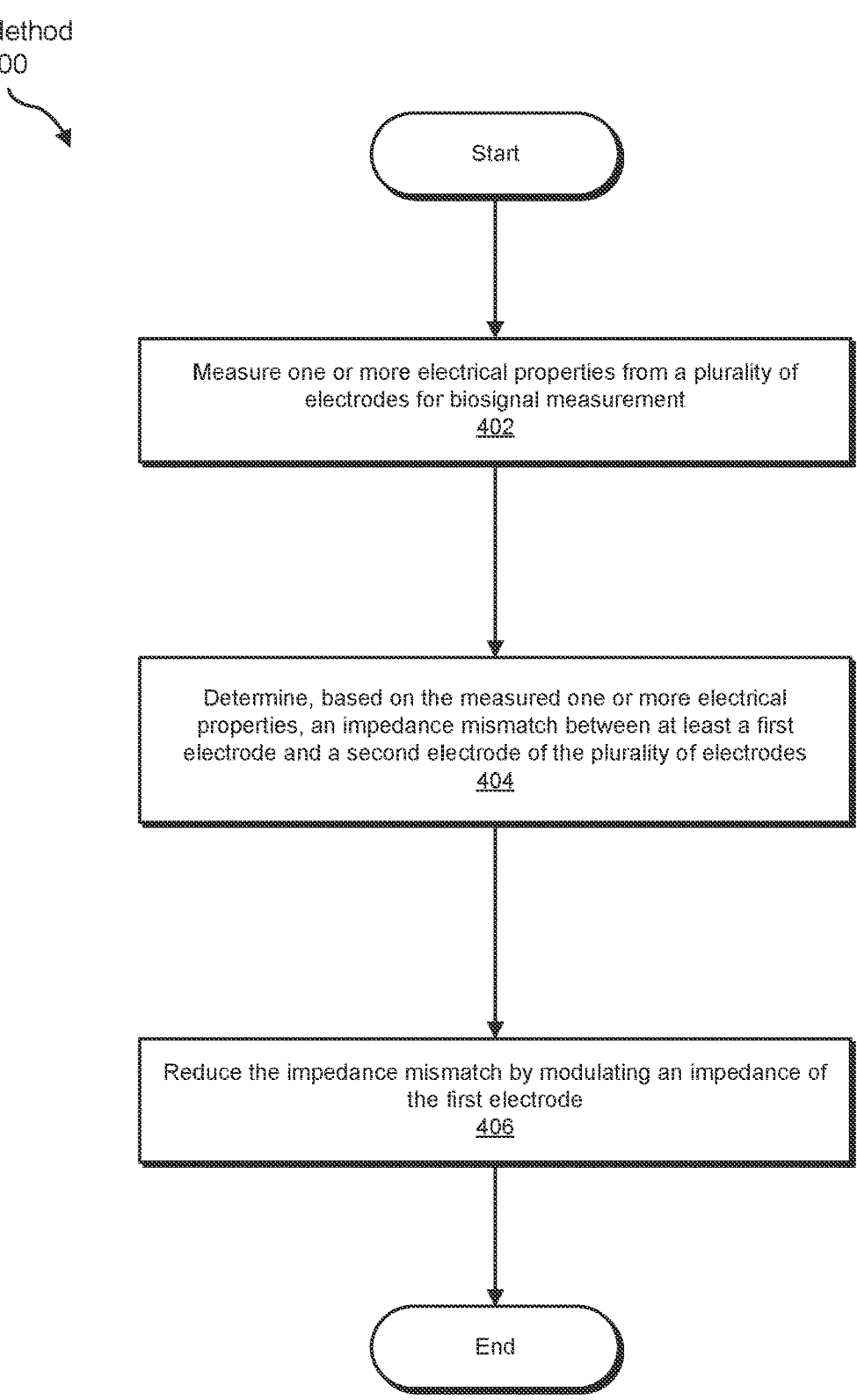
FIG. 4 is a flow diagram of an exemplary method for compensating for mismatches in biosensor electrodes.

Turning now to FIG. 4, FIG. 4 is a flow diagram of an exemplary computer-implemented method 400 for mismatch compensation for biosensor electrodes. The steps shown in FIG. 4 may be performed by any suitable computer-executable code and/or computing system, including the system(s) illustrated in FIGS. 1, 2A-2C, 3A-3C, 8A-8B, and/or 9A-9B. In one example, each of the steps shown in FIG. 4 may represent an algorithm whose structure includes and/or is represented by multiple sub-steps, examples of which will be provided in greater detail below.

As illustrated in FIG. 4, at step 402 one or more of the systems described herein may measure one or more electrical properties from a plurality of electrodes for biosignal measurement. For example, electrical property measurement circuit 140 may measure one or more electrical properties from electrodes 110 (e.g., at least one of electrode 110A, electrode 110B, electrode 110C, and electrode 110D). In some examples, the electrical properties may include impedance, phase, and/or DC offset (e.g., an electrode half-cell DC offset which may indicate interface quality) of each electrode at run time.

The systems described herein may perform step 402 in a variety of ways. In one example, measuring the one or more electrical properties may include measuring a first impedance of the first electrode and a second impedance of the second electrode. For example, electrical property measurement circuit 140 may directly measure the impedances of electrodes 110. In some examples, electrical property measurement circuit 140 may include out-of-band high frequency components for impedance measurements.

Figure 5:
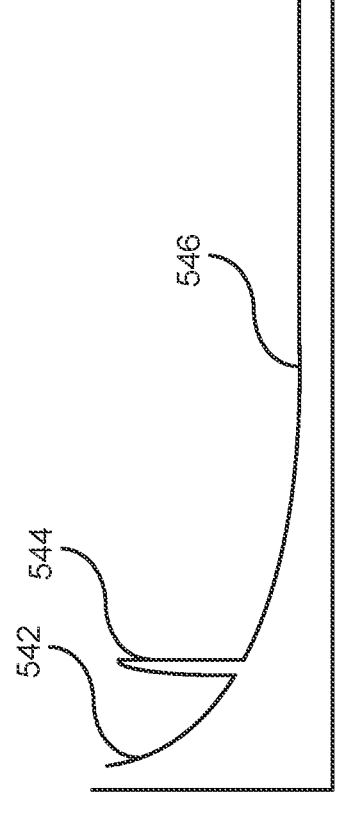
FIG. 5 is a graph of an example noise spectrum.

In some examples, measuring the one or more electrical properties may include measuring a signal using the plurality of electrodes. For example, rather than directly measuring impedances, electrical property measurement circuit 140 may measure an effect of impedance mismatch, such as noise within a measured biosignal. In some examples, detecting the noise within the biosignal may include measuring a common mode noise, for instance using an analog-to-digital converter (ADC) or a multi-comparator circuitry. FIG. 5 illustrates a graph 500 of an example noise spectrum from an input signal (e.g., signal measured by electrodes). In FIG. 5, the x-axis may correspond to frequency, and the y-axis may correspond to power.

In FIG. 5, an initial downward or negative slope portion 542, followed by a spike 544, followed by a flat portion 546. Flat portion 546 may correspond to white noise in the input signal. Spike 544 may correspond to PLI noise (e.g., 50/60 Hz noise). Negative slope portion 542 may correspond to electrode impedance noise. A graph 500 for each channel (e.g., electrode) of input may be analyzed with respect to other channels. In some examples, PLI magnitudes may be analyzed to determine relative impedances between channels. In other examples, negative slope portion 542 may be analyzed across channels to determine absolute impedance measurements for each channel. In some examples, electrical property measurement circuit 140 may use forward error predictions to reduce latency issues.

Returning to step 402 in FIG. 4, in some examples the second electrode may correspond to a reference electrode. As described herein, processor 130 may select one of electrodes 110 as the reference electrode based on, for instance, machine learning or other predictive analysis on the measured electrical properties to select an electrode that may be readily matched by other electrodes (e.g., via impedance modulation) and/or that may exhibit consistent good performance (e.g., having properties within a variance tolerance).

In some examples, processor 130 may select a weak electrode from the plurality of electrodes and disregard measurements from the weak electrode. For example, processor 130 may determine based on machine learning or other predictive analysis on the measured electrical properties that one or more electrodes may exhibit consistent poor performance (e.g., having properties outside of a variance tolerance) such that impedance modulation may not sufficiently overcome the poor performance and signals from the weak electrode(s) may adversely affect signal measurement. Processor 130 may disregard the weak electrode(s) by ignoring signals from the weak electrode(s) or shutting off the weak electrode(s).

In some examples, processor 130 may further manage electrodes. In fully differential systems having pairs of positive and negative electrodes, if one of a pair of differential electrodes is considered a weak electrode, a corresponding one of another pair of differential electrodes may be used. For example, in a negative electrode of a first pair is weak, processor 130 may designate a negative electrode of a second pair as also the negative electrode of the first pair.

Continuing on to step 404, one or more of the systems described herein may determine, based on the measured one or more electrical properties, an impedance mismatch between at least a first electrode and a second electrode of the plurality of electrodes. For example, processor 130 may determine an impedance mismatch amongst electrodes 110 based on the measured electrical properties.

The systems described herein may perform step 404 in a variety of ways. In one example, determining the impedance mismatch may include comparing the first impedance to the second impedance. For example, if the impedances were directly measured, processor 130 may compare the impedances of electrodes 110.

In some examples, determining the impedance mismatch may include predicting the impedance mismatch using the measured signal. As described herein, relative impedances may be inferred based on signal measurements, for example by attributing unaccounted noise (e.g., noise that has not been reduced by other noise reduction techniques) to impedance mismatches. In some examples, processor 130 may perform statistical analysis on signal chains.

At step 406 one or more of the systems described herein may reduce the impedance mismatch by modulating an impedance of the first electrode. For example, impedance modulating circuit 120 may modulate an impedance of one or more of electrodes 110 to reduce impedance mismatches. In some examples, processor 130 may provide instructions to impedance modulating circuit 120 for compensating for impedance mismatches by modulating impedances of one or more of electrodes 110.

The systems described herein may perform step 406 in a variety of ways. In one example, reducing the impedance mismatch may include modulating the impedance of the first electrode based on the comparison. For example, if the impedances were directly measured, impedance modulating circuit 120 may modulate impedance to match as much as possible the impedance of the reference electrode. In some examples, modulating the impedance may include changing a capacitance of at least the first electrode based on the impedance mismatch.

In some examples, reducing the impedance mismatch may include modulating the impedance of the first electrode based on the predicted impedance mismatch. For example, if relative impedances were determined, impedance modulating circuit 120 may modulate impedances by iteratively modulating impedances to reduce the impedance mismatches to an acceptable level. For instance, reducing the impedance mismatch may include determining an updated impedance mismatch in response to modulating the impedance of the first electrode, determining whether the updated impedance mismatch satisfies an error margin, and modulating the impedance of the first electrode in response to determining that the updated impedance mismatch does not satisfy the error margin. In some examples, impedance changes may occur minute-to-minute such that the iterative approach, which may take seconds, may respond fast enough to be effective.

In some examples, reducing the impedance mismatch may further include determining an updated impedance mismatch in response to modulating the impedance of the first electrode, determining whether the updated impedance mismatch satisfies an error margin and also reverting the modulated impedance of the first electrode in response to determining that the updated impedance mismatch does not satisfy the error margin. Reducing the impedance mismatch may include modulating the impedance of the second electrode in response to determining that the updated impedance mismatch does not satisfy the error margin. For example, modulating the impedance of a particular electrode (e.g., electrode 110B for instance) may produce limited success such that modulating the impedance of a different electrode (e.g., electrode 110A for instance), may produce better results.

In addition to reducing impedance mismatches, impedance modulating circuit 120 may also allow processing frequencies outside of a biosignal frequency range. For example, after measuring a signal using the plurality of electrodes, impedance modulating circuit 120 may downconvert the measured signal, as further described herein. For example, biosensing device 100 (e.g., via one or more of electrodes 110 and/or analog front end 150), may measure a signal that may have a plurality of signal components that are distinguishable by frequency range. Impedance modulating circuit 120 (and/or subcomponents thereof) may selectably downconvert one or more of the plurality of signal components.

In some examples, processor 130 may provide information on wearability conditions. For example, if impedance modulating circuit 120 fails to effectively compensate for impedance mismatches, the user may be informed of poor wearability conditions such that the user may adjust how biosensing device 100 is worn.

The systems and methods described herein provide for mismatch compensation for biosensor electrodes. As described herein, EMG inputs may be affected by line noise. The level of noise being introduced to the system may be related to how balanced the differential inputs are, and more specifically how much the impedance of each input differs from each other. The unbalancing of the inputs may occur naturally due to how each EMG electrode contacts the body, which affects the signal quality.

The systems and methods described herein may provide for balancing the inputs by introducing adaptive input impedance control. The unbalance of the EMG inputs may be sensed by the level of common mode noise. Depending on the noise level detected, a control mechanism may change the impedance of an EMG input until the noise level is deemed low enough.

The unbalance between EMG inputs (e.g., electrodes) may be caused by the resistive difference between the EMG inputs. The unbalance may cause a difference in ground potential and introduces common mode noise. A greater amount of common mode noise may correspond to a greater unbalance between the EMG inputs. Because the input signal may be an AC input, the capacitive properties of the device may be leveraged to do the balancing. For instance, changing the capacitive load at the input may change the cut-off frequency. A closer cut-off between two inputs may result in less potential difference, which may further result in less common mode noise contribution from the power line fundamental frequency and its harmonics.

In addition, changing the capacitive value may allow matching time constants at the differential EMG inputs. For example if a first EMG input has 10 Mohm at 1 pF and a second EMG input has 5 Mohm at 1 pF, The cut-off frequency (f=½*pi*RC), may be calculated as 15,915 Hz and 31,831 Hz respectively for the two inputs. However, changing the capacitance value for the second EMG input to 2 pF results in both time constants being the same, namely 15,915 Hz. Thus, the two inputs may be balanced.

To identify that there an unbalance, the level of the common mode noise in the instrumentational amplifier may be measured, for example with an ADC or multi-comparator circuitry with different threshold. The output of the measurement may be used as an input to identify the level of unbalance.

A control mechanism (e.g., MCU, control logic, etc.) may identify the level of unbalance and accordingly provide different compensation signals base on the measured level of unbalance. The compensation signal may be used for controlling how much the capacitance should be changed. For example, the compensation signal may be used to change the capacitance at a first EMG input. If the measured common mode noise is decreased, the appropriate EMG input was compensated. Otherwise, the capacitance at the first EMG input may be changed back and the compensation signal may be sent to change the capacitance at the second EMG input. The common mode noise may be iteratively measured to see if the compensation signal should be adjusted to reach optimal effect. The compensation signal may be sent by a digital control IF or an analog signal. The capacitance may be changed using, for example, an array of capacitors, variable capacitors, PTIC (Passive Tunable Integrated Circuits), varactor diodes, etc.

EXAMPLE EMBODIMENTS

Example 1: A method for mismatch compensation for biosensor electrodes comprising: measuring one or more electrical properties from a plurality of electrodes for biosignal measurement; determining, based on the measured one or more electrical properties, an impedance mismatch between at least a first electrode and a second electrode of the plurality of electrodes; and reducing the impedance mismatch by modulating an impedance of the first electrode.

Example 2: The method of Example 1, wherein: measuring the one or more electrical properties includes measuring a first impedance of the first electrode and a second impedance of the second electrode; determining the impedance mismatch includes comparing the first impedance to the second impedance; and reducing the impedance mismatch includes modulating the impedance of the first electrode based on the comparison.

Example 3: The method of Example 1 or 2, wherein: measuring the one or more electrical properties includes measuring a signal using the plurality of electrodes; determining the impedance mismatch includes predicting the impedance mismatch using the measured signal; and reducing the impedance mismatch includes modulating the impedance of the first electrode based on the predicted impedance mismatch.

Example 4: The method of Example 1, 2, or 3, wherein reducing the impedance mismatch further comprises: determining an updated impedance mismatch in response to modulating the impedance of the first electrode; determining whether the updated impedance mismatch satisfies an error margin; and modulating the impedance of the first electrode in response to determining that the updated impedance mismatch does not satisfy the error margin.

Example 5: The method of any of Examples 1-4, further comprising selecting a reference electrode from the plurality of electrodes based on the measured one or more electrical properties, wherein the second electrode corresponds to the reference electrode.

Example 6: The method of any of Examples 1-5, further comprising selecting a weak electrode from the plurality of electrodes and disregarding measurements from the weak electrode.

Example 7: The method of any of Examples 1-6, wherein reducing the impedance mismatch further comprises modulating the impedance of the first electrode using an impedance modulating circuit.

Example 8: The method of Example 7, wherein the impedance modulating circuit comprises one or more variable impedance blocks.

Example 9: The method of Example 7 or 8, wherein the impedance modulating circuit comprises one or more switched capacitors.

Example 10: The method of Example 7, 8, or 9, further comprising: measuring a signal using the plurality of electrodes; and downconverting the measured signal using the impedance modulating circuit.

Example 11: A biosensing device comprising: a plurality of electrodes for biosignal measurement; an electrical property measurement circuit; an impedance modulating circuit; and at least one physical processor configured to: measure, using the electrical property measurement circuit, one or more electrical properties from the plurality of electrodes; determine, based on the measured one or more electrical properties, an impedance mismatch between at least a first electrode and a second electrode of the plurality of electrodes; and reduce the impedance mismatch by modulating an impedance of the first electrode using the impedance modulating circuit.

Example 12: The biosensing device of Example 11, wherein: measuring the one or more electrical properties includes measuring a first impedance of the first electrode and a second impedance of the second electrode; determining the impedance mismatch includes comparing the first impedance to the second impedance; and reducing the impedance mismatch includes modulating the impedance of the first electrode based on the comparison.

Example 13: The biosensing device of Example 11 or 12, wherein: measuring the one or more electrical properties includes measuring a signal using the plurality of electrodes; determining the impedance mismatch includes predicting the impedance mismatch using the measured signal; and reducing the impedance mismatch includes modulating the impedance of the first electrode based on the predicted impedance mismatch.

Example 14: The biosensing device of Example 11, 12, or 13, wherein reducing the impedance mismatch further comprises: determining an updated impedance mismatch in response to modulating the impedance of the first electrode; determining whether the updated impedance mismatch satisfies an error margin; and modulating the impedance of the first electrode in response to determining that the updated impedance mismatch does not satisfy the error margin.

Example 15: The biosensing device of any of Examples 11-14, further comprising selecting a reference electrode from the plurality of electrodes based on the measured one or more electrical properties, wherein the second electrode corresponds to the reference electrode.

Example 16: The biosensing device of any of Examples 11-15, further comprising selecting a weak electrode from the plurality of electrodes and disregarding measurements from the weak electrode.

Example 17: The biosensing device of any of Examples 11-16, wherein the impedance modulating circuit comprises one or more variable impedance blocks.

Example 18: The biosensing device of any of Examples 11-17, wherein the impedance modulating circuit comprises one or more switched capacitors.

Example 19: The biosensing device of any of Examples 11-18, further comprising: measuring a signal using the plurality of electrodes; and downconverting the measured signal using the impedance modulating circuit.

Example 20: A system comprising: at least one physical processor; physical memory comprising computer-executable instructions; and a biosensing device comprising: a plurality of electrodes for biosignal measurement; an electrical property measurement circuit; and an impedance modulating circuit; wherein the at least one physical processor is configured to: measure, using the electrical property measurement circuit, one or more electrical properties from the plurality of electrodes; determine, based on the measured one or more electrical properties, an impedance mismatch between at least a first electrode and a second electrode of the plurality of electrodes; and reduce impedance mismatch by modulating an impedance of the first electrode using the impedance modulating circuit.

Embodiments of the present disclosure may include or be implemented in conjunction with various types of artificial-reality systems. Artificial reality is a form of reality that has been adjusted in some manner before presentation to a user, which may include, for example, a virtual reality, an augmented reality, a mixed reality, a hybrid reality, or some combination and/or derivative thereof. Artificial-reality content may include completely computer-generated content or computer-generated content combined with captured (e.g., real-world) content. The artificial-reality content may include video, audio, haptic feedback, or some combination thereof, any of which may be presented in a single channel or in multiple channels (such as stereo video that produces a three-dimensional (3D) effect to the viewer). Additionally, in some embodiments, artificial reality may also be associated with applications, products, accessories, services, or some combination thereof, that are used to, for example, create content in an artificial reality and/or are otherwise used in (e.g., to perform activities in) an artificial reality.

Artificial-reality systems may be implemented in a variety of different form factors and configurations. Some artificial-reality systems may be designed to work without near-eye displays (NEDs). Other artificial-reality systems may include an NED that also provides visibility into the real world (such as, e.g., augmented-reality system 600 in FIG. 6) or that visually immerses a user in an artificial reality (such as, e.g., virtual-reality system 700 in FIG. 7). While some artificial-reality devices may be self-contained systems, other artificial-reality devices may communicate and/or coordinate with external devices to provide an artificial-reality experience to a user. Examples of such external devices include handheld controllers, mobile devices, desktop computers, devices worn by a user, devices worn by one or more other users, and/or any other suitable external system.

Figure 6:
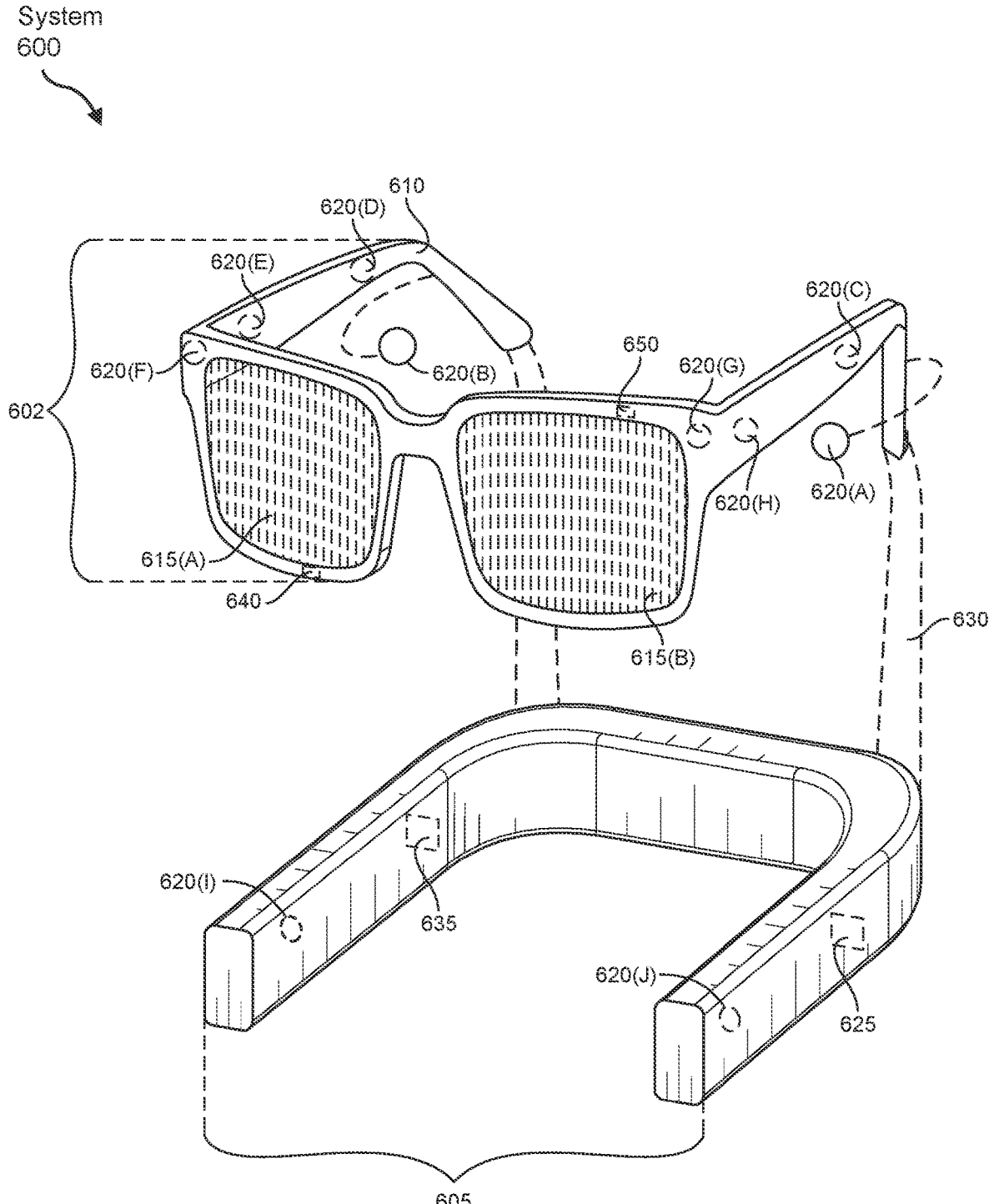
FIG. 6 is an illustration of exemplary augmented-reality glasses that may be used in connection with embodiments of this disclosure.
Figure 7:
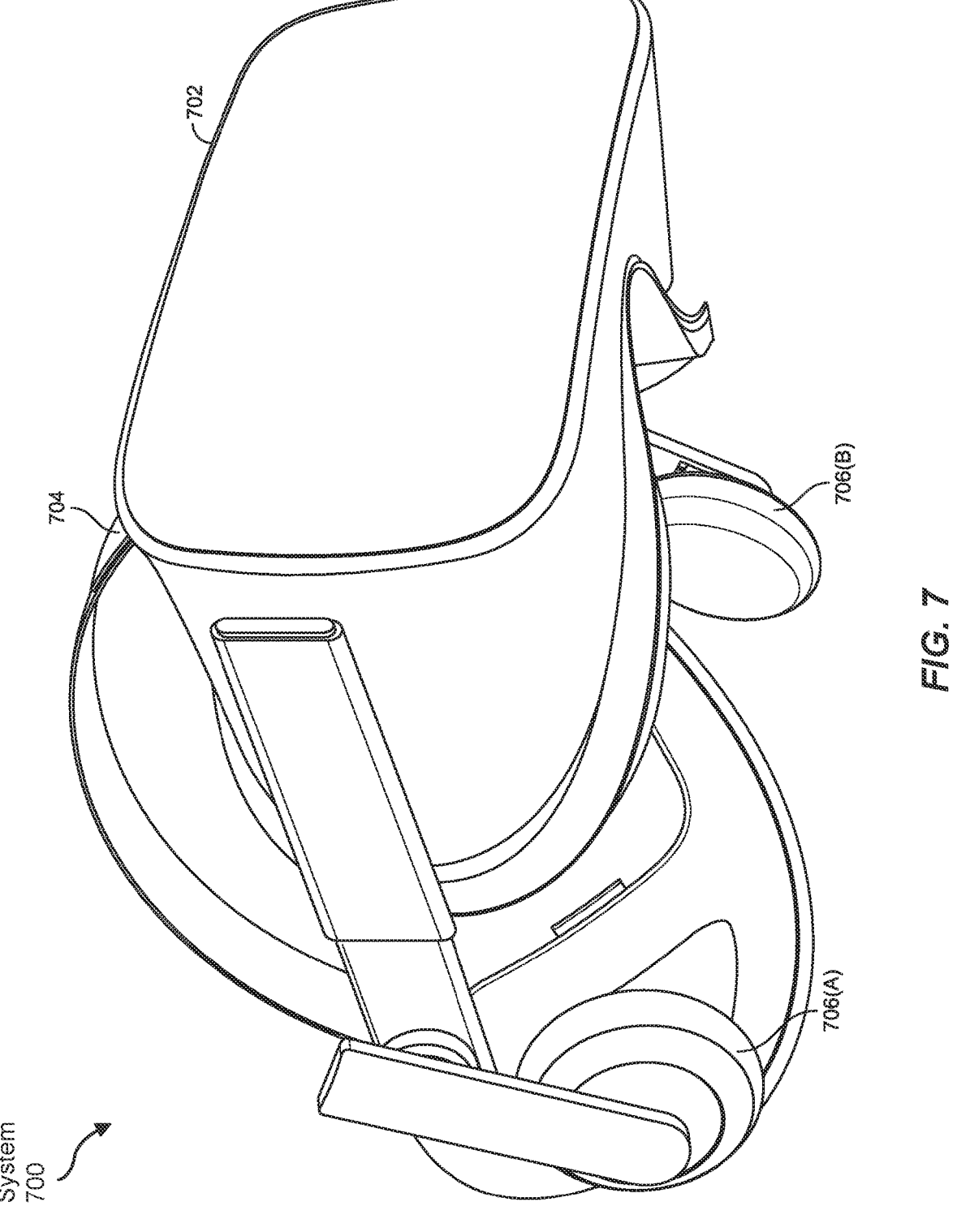
FIG. 7 is an illustration of an exemplary virtual-reality headset that may be used in connection with embodiments of this disclosure.

Turning to FIG. 6, augmented-reality system 600 may include an eyewear device 602 with a frame 610 configured to hold a left display device 615(A) and a right display device 615(B) in front of a user's eyes. Display devices 615(A) and 615(B) may act together or independently to present an image or series of images to a user. While augmented-reality system 600 includes two displays, embodiments of this disclosure may be implemented in augmented-reality systems with a single NED or more than two NEDs.

In some embodiments, augmented-reality system 600 may include one or more sensors, such as sensor 640. Sensor 640 may generate measurement signals in response to motion of augmented-reality system 600 and may be located on substantially any portion of frame 610. Sensor 640 may represent one or more of a variety of different sensing mechanisms, such as a position sensor, an inertial measurement unit (IMU), a depth camera assembly, a structured light emitter and/or detector, or any combination thereof. In some embodiments, augmented-reality system 600 may or may not include sensor 640 or may include more than one sensor. In embodiments in which sensor 640 includes an IMU, the IMU may generate calibration data based on measurement signals from sensor 640. Examples of sensor 640 may include, without limitation, accelerometers, gyroscopes, magnetometers, other suitable types of sensors that detect motion, sensors used for error correction of the IMU, or some combination thereof.

In some examples, augmented-reality system 600 may also include a microphone array with a plurality of acoustic transducers 620(A)-620(J), referred to collectively as acoustic transducers 620. Acoustic transducers 620 may represent transducers that detect air pressure variations induced by sound waves. Each acoustic transducer 620 may be configured to detect sound and convert the detected sound into an electronic format (e.g., an analog or digital format). The microphone array in FIG. 6 may include, for example, ten acoustic transducers: 620(A) and 620(B), which may be designed to be placed inside a corresponding ear of the user, acoustic transducers 620(C), 620(D), 620(E), 620(F), 620 (G), and 620(H), which may be positioned at various locations on frame 610, and/or acoustic transducers 620(I) and 620(J), which may be positioned on a corresponding neckband 605.

In some embodiments, one or more of acoustic transducers 620(A)-(J) may be used as output transducers (e.g., speakers). For example, acoustic transducers 620(A) and/or 620(B) may be earbuds or any other suitable type of headphone or speaker.

The configuration of acoustic transducers 620 of the microphone array may vary. While augmented-reality system 600 is shown in FIG. 6 as having ten acoustic transducers 620, the number of acoustic transducers 620 may be greater or less than ten. In some embodiments, using higher numbers of acoustic transducers 620 may increase the amount of audio information collected and/or the sensitivity and accuracy of the audio information. In contrast, using a lower number of acoustic transducers 620 may decrease the computing power required by an associated controller 650 to process the collected audio information. In addition, the position of each acoustic transducer 620 of the microphone array may vary. For example, the position of an acoustic transducer 620 may include a defined position on the user, a defined coordinate on frame 610, an orientation associated with each acoustic transducer 620, or some combination thereof.

Acoustic transducers 620(A) and 620(B) may be positioned on different parts of the user's ear, such as behind the pinna, behind the tragus, and/or within the auricle or fossa. Or, there may be additional acoustic transducers 620 on or surrounding the ear in addition to acoustic transducers 620 inside the ear canal. Having an acoustic transducer 620 positioned next to an ear canal of a user may enable the microphone array to collect information on how sounds arrive at the ear canal. By positioning at least two of acoustic transducers 620 on either side of a user's head (e.g., as binaural microphones), augmented-reality device 600 may simulate binaural hearing and capture a 3D stereo sound field around about a user's head. In some embodiments, acoustic transducers 620(A) and 620(B) may be connected to augmented-reality system 600 via a wired connection 630, and in other embodiments acoustic transducers 620(A) and 620(B) may be connected to augmented-reality system 600 via a wireless connection (e.g., a BLUETOOTH connection). In still other embodiments, acoustic transducers 620(A) and 620(B) may not be used at all in conjunction with augmented-reality system 600.

Acoustic transducers 620 on frame 610 may be positioned in a variety of different ways, including along the length of the temples, across the bridge, above or below display devices 615(A) and 615(B), or some combination thereof. Acoustic transducers 620 may also be oriented such that the microphone array is able to detect sounds in a wide range of directions surrounding the user wearing the augmented-reality system 600. In some embodiments, an optimization process may be performed during manufacturing of augmented-reality system 600 to determine relative positioning of each acoustic transducer 620 in the microphone array.

In some examples, augmented-reality system 600 may include or be connected to an external device (e.g., a paired device), such as neckband 605. Neckband 605 generally represents any type or form of paired device. Thus, the following discussion of neckband 605 may also apply to various other paired devices, such as charging cases, smart watches, smart phones, wrist bands, other wearable devices, hand-held controllers, tablet computers, laptop computers, other external compute devices, etc.

As shown, neckband 605 may be coupled to eyewear device 602 via one or more connectors. The connectors may be wired or wireless and may include electrical and/or non-electrical (e.g., structural) components. In some cases, eyewear device 602 and neckband 605 may operate independently without any wired or wireless connection between them. While FIG. 6 illustrates the components of eyewear device 602 and neckband 605 in example locations on eyewear device 602 and neckband 605, the components may be located elsewhere and/or distributed differently on eyewear device 602 and/or neckband 605. In some embodiments, the components of eyewear device 602 and neckband 605 may be located on one or more additional peripheral devices paired with eyewear device 602, neckband 605, or some combination thereof.

Pairing external devices, such as neckband 605, with augmented-reality eyewear devices may enable the eyewear devices to achieve the form factor of a pair of glasses while still providing sufficient battery and computation power for expanded capabilities. Some or all of the battery power, computational resources, and/or additional features of augmented-reality system 600 may be provided by a paired device or shared between a paired device and an eyewear device, thus reducing the weight, heat profile, and form factor of the eyewear device overall while still retaining desired functionality. For example, neckband 605 may allow components that would otherwise be included on an eyewear device to be included in neckband 605 since users may tolerate a heavier weight load on their shoulders than they would tolerate on their heads. Neckband 605 may also have a larger surface area over which to diffuse and disperse heat to the ambient environment. Thus, neckband 605 may allow for greater battery and computation capacity than might otherwise have been possible on a stand-alone eyewear device. Since weight carried in neckband 605 may be less invasive to a user than weight carried in eyewear device 602, a user may tolerate wearing a lighter eyewear device and carrying or wearing the paired device for greater lengths of time than a user would tolerate wearing a heavy standalone eyewear device, thereby enabling users to more fully incorporate artificial-reality environments into their day-to-day activities.

Neckband 605 may be communicatively coupled with eyewear device 602 and/or to other devices. These other devices may provide certain functions (e.g., tracking, localizing, depth mapping, processing, storage, etc.) to augmented-reality system 600. In the embodiment of FIG. 6, neckband 605 may include two acoustic transducers (e.g., 620(I) and 620(J)) that are part of the microphone array (or potentially form their own microphone subarray). Neckband 605 may also include a controller 625 and a power source 635.

Acoustic transducers 620(I) and 620(J) of neckband 605 may be configured to detect sound and convert the detected sound into an electronic format (analog or digital). In the embodiment of FIG. 6, acoustic transducers 620(I) and 620(J) may be positioned on neckband 605, thereby increasing the distance between the neckband acoustic transducers 620(I) and 620(J) and other acoustic transducers 620 positioned on eyewear device 602. In some cases, increasing the distance between acoustic transducers 620 of the microphone array may improve the accuracy of beamforming performed via the microphone array. For example, if a sound is detected by acoustic transducers 620(C) and 620(D) and the distance between acoustic transducers 620(C) and 620 (D) is greater than, e.g., the distance between acoustic transducers 620(D) and 620(E), the determined source location of the detected sound may be more accurate than if the sound had been detected by acoustic transducers 620(D) and 620(E).

Controller 625 of neckband 605 may process information generated by the sensors on neckband 605 and/or augmented-reality system 600. For example, controller 625 may process information from the microphone array that describes sounds detected by the microphone array. For each detected sound, controller 625 may perform a direction-of-arrival (DOA) estimation to estimate a direction from which the detected sound arrived at the microphone array. As the microphone array detects sounds, controller 625 may populate an audio data set with the information. In embodiments in which augmented-reality system 600 includes an inertial measurement unit, controller 625 may compute all inertial and spatial calculations from the IMU located on eyewear device 602. A connector may convey information between augmented-reality system 600 and neckband 605 and between augmented-reality system 600 and controller 625. The information may be in the form of optical data, electrical data, wireless data, or any other transmittable data form. Moving the processing of information generated by augmented-reality system 600 to neckband 605 may reduce weight and heat in eyewear device 602, making it more comfortable to the user.

Power source 635 in neckband 605 may provide power to eyewear device 602 and/or to neckband 605. Power source 635 may include, without limitation, lithium ion batteries, lithium-polymer batteries, primary lithium batteries, alkaline batteries, or any other form of power storage. In some cases, power source 635 may be a wired power source. Including power source 635 on neckband 605 instead of on eyewear device 602 may help better distribute the weight and heat generated by power source 635.

As noted, some artificial-reality systems may, instead of blending an artificial reality with actual reality, substantially replace one or more of a user's sensory perceptions of the real world with a virtual experience. One example of this type of system is a head-worn display system, such as virtual-reality system 700 in FIG. 7, that mostly or completely covers a user's field of view. Virtual-reality system 700 may include a front rigid body 702 and a band 704 shaped to fit around a user's head. Virtual-reality system 700 may also include output audio transducers 706(A) and 706(B). Furthermore, while not shown in FIG. 7, front rigid body 702 may include one or more electronic elements, including one or more electronic displays, one or more inertial measurement units (IMUs), one or more tracking emitters or detectors, and/or any other suitable device or system for creating an artificial-reality experience.

Artificial-reality systems may include a variety of types of visual feedback mechanisms. For example, display devices in augmented-reality system 600 and/or virtual-reality system 700 may include one or more liquid crystal displays (LCDs), light emitting diode (LED) displays, microLED displays, organic LED (OLED) displays, digital light project (DLP) micro-displays, liquid crystal on silicon (LCoS) micro-displays, and/or any other suitable type of display screen. These artificial-reality systems may include a single display screen for both eyes or may provide a display screen for each eye, which may allow for additional flexibility for varifocal adjustments or for correcting a user's refractive error. Some of these artificial-reality systems may also include optical subsystems having one or more lenses (e.g., concave or convex lenses, Fresnel lenses, adjustable liquid lenses, etc.) through which a user may view a display screen. These optical subsystems may serve a variety of purposes, including to collimate (e.g., make an object appear at a greater distance than its physical distance), to magnify (e.g., make an object appear larger than its actual size), and/or to relay (to, e.g., the viewer's eyes) light. These optical subsystems may be used in a non-pupil-forming architecture (such as a single lens configuration that directly collimates light but results in so-called pincushion distortion) and/or a pupil-forming architecture (such as a multi-lens configuration that produces so-called barrel distortion to nullify pincushion distortion).

In addition to or instead of using display screens, some of the artificial-reality systems described herein may include one or more projection systems. For example, display devices in augmented-reality system 600 and/or virtual-reality system 700 may include micro-LED projectors that project light (using, e.g., a waveguide) into display devices, such as clear combiner lenses that allow ambient light to pass through. The display devices may refract the projected light toward a user's pupil and may enable a user to simultaneously view both artificial-reality content and the real world. The display devices may accomplish this using any of a variety of different optical components, including waveguide components (e.g., holographic, planar, diffractive, polarized, and/or reflective waveguide elements), light-manipulation surfaces and elements (such as diffractive, reflective, and refractive elements and gratings), coupling elements, etc. Artificial-reality systems may also be configured with any other suitable type or form of image projection system, such as retinal projectors used in virtual retina displays.

The artificial-reality systems described herein may also include various types of computer vision components and subsystems. For example, augmented-reality system 600 and/or virtual-reality system 700 may include one or more optical sensors, such as two-dimensional (2D) or 3D cameras, structured light transmitters and detectors, time-of-flight depth sensors, single-beam or sweeping laser rangefinders, 3D LiDAR sensors, and/or any other suitable type or form of optical sensor. An artificial-reality system may process data from one or more of these sensors to identify a location of a user, to map the real world, to provide a user with context about real-world surroundings, and/or to perform a variety of other functions.

The artificial-reality systems described herein may also include one or more input and/or output audio transducers. Output audio transducers may include voice coil speakers, ribbon speakers, electrostatic speakers, piezoelectric speakers, bone conduction transducers, cartilage conduction transducers, tragus-vibration transducers, and/or any other suitable type or form of audio transducer. Similarly, input audio transducers may include condenser microphones, dynamic microphones, ribbon microphones, and/or any other type or form of input transducer. In some embodiments, a single transducer may be used for both audio input and audio output.

In some embodiments, the artificial-reality systems described herein may also include tactile (i.e., haptic) feedback systems, which may be incorporated into headwear, gloves, body suits, handheld controllers, environmental devices (e.g., chairs, floormats, etc.), and/or any other type of device or system. Haptic feedback systems may provide various types of cutaneous feedback, including vibration, force, traction, texture, and/or temperature. Haptic feedback systems may also provide various types of kinesthetic feedback, such as motion and compliance. Haptic feedback may be implemented using motors, piezoelectric actuators, fluidic systems, and/or a variety of other types of feedback mechanisms. Haptic feedback systems may be implemented independent of other artificial-reality devices, within other artificial-reality devices, and/or in conjunction with other artificial-reality devices.

By providing haptic sensations, audible content, and/or visual content, artificial-reality systems may create an entire virtual experience or enhance a user's real-world experience in a variety of contexts and environments. For instance, artificial-reality systems may assist or extend a user's perception, memory, or cognition within a particular environment. Some systems may enhance a user's interactions with other people in the real world or may enable more immersive interactions with other people in a virtual world. Artificial-reality systems may also be used for educational purposes (e.g., for teaching or training in schools, hospitals, government organizations, military organizations, business enterprises, etc.), entertainment purposes (e.g., for playing video games, listening to music, watching video content, etc.), and/or for accessibility purposes (e.g., as hearing aids, visual aids, etc.). The embodiments disclosed herein may enable or enhance a user's artificial-reality experience in one or more of these contexts and environments and/or in other contexts and environments.

Figure 8A:
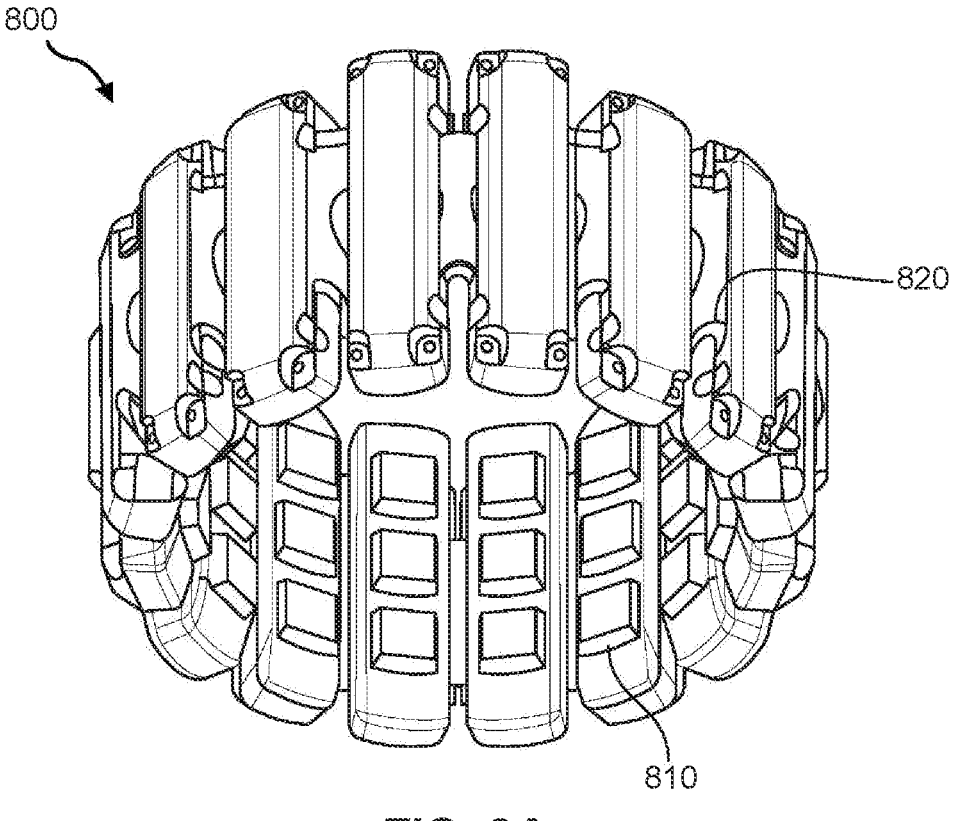
FIGS. 8A and 8B are illustrations of an exemplary human-machine interface configured to be worn around a user's lower arm or wrist.
Figure 8B:
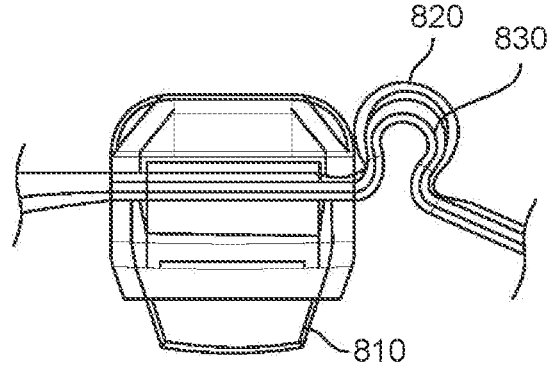

FIG. 8A illustrates an exemplary human-machine interface (also referred to herein as an EMG control interface) configured to be worn around a user's lower arm or wrist as a wearable system 800. In this example, wearable system 800 may include sixteen neuromuscular sensors 810 (e.g., EMG sensors) arranged circumferentially around an elastic band 820 with an interior surface 830 configured to contact a user's skin. However, any suitable number of neuromuscular sensors may be used. The number and arrangement of neuromuscular sensors may depend on the particular application for which the wearable device is used. For example, a wearable armband or wristband can be used to generate control information for controlling an augmented reality system, a robot, controlling a vehicle, scrolling through text, controlling a virtual avatar, or any other suitable control task. As shown, the sensors may be coupled together using flexible electronics incorporated into the wireless device. FIG. 8B illustrates a cross-sectional view through one of the sensors of the wearable device shown in FIG. 8A. In some embodiments, the output of one or more of the sensing components can be optionally processed using hardware signal processing circuitry (e.g., to perform amplification, filtering, and/or rectification). In other embodiments, at least some signal processing of the output of the sensing components can be performed in software. Thus, signal processing of signals sampled by the sensors can be performed in hardware, software, or by any suitable combination of hardware and software, as aspects of the technology described herein are not limited in this respect. A non-limiting example of a signal processing chain used to process recorded data from sensors 810 is discussed in more detail below with reference to FIGS. 9A and 9B.

Figures 9A, 9B:
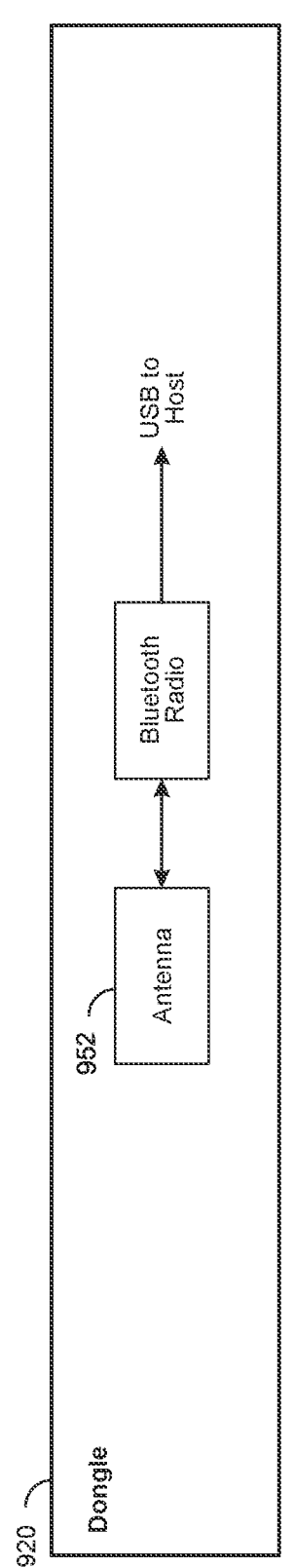
FIGS. 9A and 9B are illustrations of an exemplary schematic diagram with internal components of a wearable system.

FIGS. 9A and 9B illustrate an exemplary schematic diagram with internal components of a wearable system with EMG sensors. As shown, the wearable system may include a wearable portion 910 (FIG. 9A) and a dongle portion 920 (FIG. 9B) in communication with the wearable portion 910 (e.g., via BLUETOOTH or another suitable wireless communication technology). As shown in FIG. 9A, the wearable portion 910 may include skin contact electrodes 911, examples of which are described in connection with FIGS. 8A and 8B. The output of the skin contact electrodes 911 may be provided to analog front end 930, which may be configured to perform analog processing (e.g., amplification, noise reduction, filtering, etc.) on the recorded signals. The processed analog signals may then be provided to analog-to-digital converter 932, which may convert the analog signals to digital signals that can be processed by one or more computer processors. An example of a computer processor that may be used in accordance with some embodiments is microcontroller (MCU) 934, illustrated in FIG. 9A. As shown, MCU 934 may also include inputs from other sensors (e.g., IMU sensor 940), and power and battery module 942. The output of the processing performed by MCU 934 may be provided to antenna 950 for transmission to dongle portion 920 shown in FIG. 9B.

Dongle portion 920 may include antenna 952, which may be configured to communicate with antenna 950 included as part of wearable portion 910. Communication between antennas 950 and 952 may occur using any suitable wireless technology and protocol, non-limiting examples of which include radiofrequency signaling and BLUETOOTH. As shown, the signals received by antenna 952 of dongle portion 920 may be provided to a host computer for further processing, display, and/or for effecting control of a particular physical or virtual object or objects.

Although the examples provided with reference to FIGS. 8A-8B and FIGS. 9A-9B are discussed in the context of interfaces with EMG sensors, the techniques described herein for reducing electromagnetic interference can also be implemented in wearable interfaces with other types of sensors including, but not limited to, mechanomyography (MMG) sensors, sonomyography (SMG) sensors, and electrical impedance tomography (EIT) sensors. The techniques described herein for reducing electromagnetic interference can also be implemented in wearable interfaces that communicate with computer hosts through wires and cables (e.g., USB cables, optical fiber cables, etc.).

In some examples, the term "memory device" generally refers to any type or form of volatile or non-volatile storage device or medium capable of storing data and/or computer-readable instructions. In one example, a memory device may store, load, and/or maintain one or more of the modules described herein. Examples of memory devices include, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In some examples, the term "physical processor" generally refers to any type or form of hardware-implemented processing unit capable of interpreting and/or executing computer-readable instructions. In one example, a physical processor may access and/or modify one or more modules stored in the above-described memory device. Examples of physical processors include, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

In some embodiments, the term "computer-readable medium" generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the present disclosure. The embodiments disclosed herein should be considered in all respects illustrative and not restrictive. Reference should be made to the appended claims and their equivalents in determining the scope of the present disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising".

What is claimed is:

1. A method comprising:
measuring one or more electrical properties from a plurality of electrodes for biosignal measurement;
selecting a reference electrode from the plurality of electrodes based on the measured one or more electrical properties, wherein a second electrode corresponds to the reference electrode;
determining, based on the measured one or more electrical properties, an impedance mismatch between at least a first electrode and the second electrode of the plurality of electrodes; and
reducing the impedance mismatch by modulating an impedance of the first electrode.

2. The method of claim 1, wherein:
measuring the one or more electrical properties includes measuring a first impedance of the first electrode and a second impedance of the second electrode;
determining the impedance mismatch includes comparing the first impedance to the second impedance; and
reducing the impedance mismatch includes modulating the impedance of the first electrode based on the comparison.

3. The method of claim 1, wherein:
measuring the one or more electrical properties includes measuring a signal using the plurality of electrodes;
determining the impedance mismatch includes predicting the impedance mismatch using the measured signal; and
reducing the impedance mismatch includes modulating the impedance of the first electrode based on the predicted impedance mismatch.

4. The method of claim 1, wherein reducing the impedance mismatch further comprises:
determining an updated impedance mismatch in response to modulating the impedance of the first electrode;
determining whether the updated impedance mismatch satisfies an error margin; and
modulating the impedance of the first electrode in response to determining that the updated impedance mismatch does not satisfy the error margin.

5. The method of claim 1, further comprising selecting a weak electrode from the plurality of electrodes and disregarding measurements from the weak electrode.

6. The method of claim 1, wherein reducing the impedance mismatch further comprises modulating the impedance of the first electrode using an impedance modulating circuit.

7. The method of claim 6, wherein the impedance modulating circuit comprises one or more variable impedance blocks.

8. The method of claim 6, wherein the impedance modulating circuit comprises one or more switched capacitors.

9. The method of claim 6, further comprising:
measuring a signal using the plurality of electrodes; and downconverting the measured signal using the impedance modulating circuit.

10. A biosensing device comprising:
a plurality of electrodes for biosignal measurement;
an electrical property measurement circuit;
an impedance modulating circuit; and
at least one physical processor configured to:
measure, using the electrical property measurement circuit, one or more electrical properties from the plurality of electrodes;
select a reference electrode from the plurality of electrodes based on the measured one or more electrical properties, wherein a second electrode corresponds to the reference electrode;
determine, based on the measured one or more electrical properties, an impedance mismatch between at least a first electrode and the second electrode of the plurality of electrodes; and
reduce the impedance mismatch by modulating an impedance of the first electrode using the impedance modulating circuit.

11. The biosensing device of claim 10, wherein:
measuring the one or more electrical properties includes measuring a first impedance of the first electrode and a second impedance of the second electrode;
determining the impedance mismatch includes comparing the first impedance to the second impedance; and
reducing the impedance mismatch includes modulating the impedance of the first electrode based on the comparison.

12. The biosensing device of claim 10, wherein:
measuring the one or more electrical properties includes measuring a signal using the plurality of electrodes;
determining the impedance mismatch includes predicting the impedance mismatch using the measured signal; and
reducing the impedance mismatch includes modulating the impedance of the first electrode based on the predicted impedance mismatch.

13. The biosensing device of claim 10, wherein reducing the impedance mismatch further comprises:
determining an updated impedance mismatch in response to modulating the impedance of the first electrode;
determining whether the updated impedance mismatch satisfies an error margin; and
modulating the impedance of the first electrode in response to determining that the updated impedance mismatch does not satisfy the error margin.

14. The biosensing device of claim 10, further comprising selecting a weak electrode from the plurality of electrodes and disregarding measurements from the weak electrode.

15. The biosensing device of claim 10, wherein the impedance modulating circuit comprises one or more variable impedance blocks.

16. The biosensing device of claim 10, wherein the impedance modulating circuit comprises one or more switched capacitors.

17. The biosensing device of claim 10, further comprising:
measuring a signal using the plurality of electrodes; and
downconverting the measured signal using the impedance modulating circuit.

18. A system comprising:
at least one physical processor;
physical memory comprising computer-executable instructions; and
a biosensing device comprising:

a plurality of electrodes for biosignal measurement;

an electrical property measurement circuit; and an impedance modulating circuit;

wherein the at least one physical processor is configured to:

measure, using the electrical property measurement circuit, one or more electrical properties from the plurality of electrodes;

select a reference electrode from the plurality of electrodes based on the measured one or more electrical properties, wherein a second electrode corresponds to the reference electrode;

determine, based on the measured one or more electrical properties, an impedance mismatch between at least a first electrode and the second electrode of the plurality of electrodes; and reduce the impedance mismatch by modulating an impedance of the first electrode using the impedance modulating circuit.

19. The system of claim 18, wherein:

measuring the one or more electrical properties includes measuring a first impedance of the first electrode and a second impedance of the second electrode;

determining the impedance mismatch includes comparing the first impedance to the second impedance; and reducing the impedance mismatch includes modulating the impedance of the first electrode based on the comparison.

20. The system of claim 18, wherein:

measuring the one or more electrical properties includes measuring a signal using the plurality of electrodes;

determining the impedance mismatch includes predicting the impedance mismatch using the measured signal; and reducing the impedance mismatch includes modulating the impedance of the first electrode based on the predicted impedance mismatch.

\* \* \* \* \*